United States Patent [19]
Miyata et al.

[11] Patent Number: 6,083,501
[45] Date of Patent: Jul. 4, 2000

[54] DRUG FOR PREVENTION AND THERAPY OF DISEASES CAUSED BY FIBRINOID FORMATION OR THROMBUS FORMATION IN THE LUNG AND MODEL ANIMALS OF THE DISEASES

[75] Inventors: Masayuki Miyata; Reiji Kasukawa, both of Fukushima; Masanobu Naruto, Kamakura; Nobutaka Ida, Kamakura; Yu-ichiro Sato, Kamakura; Katsuaki Kojima, Yokohama; Nobuo Ida, Machida, all of Japan

[73] Assignee: Toray Industries, Inc., Tokyo, Japan

[21] Appl. No.: 08/592,341

[22] PCT Filed: Jun. 6, 1995

[86] PCT No.: PCT/JP95/01115

§ 371 Date: Mar. 14, 1996

§ 102(e) Date: Mar. 14, 1996

[87] PCT Pub. No.: WO95/33483

PCT Pub. Date: Dec. 14, 1995

[30] Foreign Application Priority Data

Jun. 7, 1995 [JP] Japan .................................... 6-124932

[51] Int. Cl.[7] ...................... A61K 39/395; C07C 59/147; A01N 37/08; C07K 16/00
[52] U.S. Cl. ...................................... 424/158.1; 424/283.1; 530/388.23; 530/399; 435/63; 514/573; 549/422; 554/117; 554/118; 554/214; 560/120
[58] Field of Search .............................. 530/388.23, 399; 424/283.1; 435/63; 514/573; 549/122; 554/117, 118, 214; 560/121

[56] References Cited

U.S. PATENT DOCUMENTS

| | | | |
|---|---|---|---|
| 5,135,955 | 8/1992 | Campbell et al. | 514/654 |
| 5,162,361 | 11/1992 | Rosenthal | 514/396 |
| 5,271,931 | 12/1993 | Lotz | 424/85.2 |
| 5,300,292 | 4/1994 | Ulich | 424/85.2 |
| 5,376,368 | 12/1994 | Ulich | 424/85.2 |

OTHER PUBLICATIONS van der Poll, T. et al. J. Exp. Med; 179: 1253–1259, 1994.

Norioka, K. et al. Auto Immunity, 7: 41–50, 1990.

Wakefield, Venous Thrombus Arteriosclerosis Thrombosisal Vascular Bio 15, 2, 1995 258–268.

Waldman, T Science vol. 252 Jun. 21, 1991 pp. 1657–1662.

Hams, Tibtech Therapeutic Abs Coming of age Feb. 1993 vol. 11 pp. 42–44.

Samad, F et al Stimulation of Chick hepatocyte fibronectin production by fibroblast–conditioned medium Biochim Biophys ACTA 1181 (3) 1993 207–213.

*Primary Examiner*—Paula K. Hutzell
*Assistant Examiner*—Geetha P. Bansal
*Attorney, Agent, or Firm*—Birch, Stewart, Kolasch & Birch, LLP

[57] ABSTRACT

A drug for prevention and therapy of diseases caused by fibrinoid formation or thrombus formation, as well as a model animal of fibrinoid formation or thrombus formation in the lung is disclosed. The drug for preventing and treating diseases caused by fibrinoid formation or thrombus formation in the lung according to the present invention comprises an inhibitor of interleukin 6 as an effective ingredient. The model animal of the diseases caused by fibrinoid formation or thrombus formation in the lung is a rat in which fibrinoid formation or thrombus formation actually occurs by induction with interleukin 6.

18 Claims, 2 Drawing Sheets

DRUG FOR PREVENTION AND THERAPY OF DISEASES CAUSED BY FIBRINOID FORMATION OR THROMBUS FORMATION IN THE LUNG AND MODEL ANIMALS OF THE DISEASES

TECHNICAL FIELD

The present invention relates to a drug for prevention and therapy of diseases caused by fibrinoid formation or thrombus formation in the lung, as well as to model animals of these diseases.

BACKGROUND ART

Pulmonary heart disease (cor pulmonale) is the state showing right ventricular pressure load or dysfunction of right ventricle by increase in pulmonary vascular resistance caused by diseases of lung parenchyma, pulmonary vascular diseases or extrapulmonary diseases which cause alveolar hypoventilation. Based on clinical progress and pathologic state, pulmonary heart disease is classified into three groups, that is, acute pulmonary heart, subacute pulmonary heart and chronic pulmonary heart, and the type of primary diseases of the three groups are different from each other. The representative cause of acute pulmonary heart is pulmonary thromboembolism in which right ventricle is prominently dilated without the time of presenting right ventricular hypertrophy, followed by right heart failure. The causes of subacute pulmonary heart disease include multiple or recurrent lung embolism, but its pathologic state is similar to that of acute pulmonary heart disease. The causes of chronic pulmonary heart disease include chronic occlusive pulmonary disease and pulmonary hypertension. Chronic pulmonary heart disease accompanies hyperplasia of right ventricular heart muscle, respiratory difficulty when moving, cardiopalmus and edema, and its prognosis is bad. Fibrinoid formation or thrombus formation in the lung plays a pivotal role in development of these pathological stage.

Current therapeutic methods for treating pulmonary heart disease are based on therapy and control of the primary diseases. There is no effective etiotropic methods and only nosotropic treatment is performed.

As for the model animals used for clarifying the pathologic state and for studying effective therapeutic method or the like, monocrotaline-treated rat models were employed as the model animal for pulmonary hypertension. This model is pathologically characterized mainly by hyperplasia of tunica media of muscular pulmonary artery, muscularization of pulmonary arteriole and hyperplasia of intraalveolar septa.

However, in the conventional monocrotaline-rat model animal, fibrinoid formation and thrombus formation in the lung are scarcely observed in the development of the diseased state, and the monocrotaline-rat model animal is positioned as a model of the so called secondary pulmonary hypertension in which pulmonary hypertension and interstitial pneumonia are complicated. Thus, the monocrotaline-rat model is insufficient for clarifying the pathologic state of testing pulmonary heart and for studying a therapeutic method of testing pulmonary heart depending on the severity of the disease. There is no promising therapeutic method for pulmonary heart.

DISCLOSURE OF THE INVENTION

An object of the present invention is to provide a drug for the prevention and therapy of diseases caused by fibrinoid formation or thrombus formation in the vascular system of the lung, such as pulmonary heart disease. Another object of the present invention is to provide a model animal for in the pulmonary heart disease caused by fibrinoid formation or thrombus formation in blood circulation of the lung.

The present inventors discovered that by administering interleukin 6 (hereinafter also referred to as "IL-6") to rats, formation of fibrinoid or thrombus in the lung is caused to develop pulmonary heart disease and that prevention and therapy of the diseases caused by fibrinoid formation or thrombus formation in the lung can be attained by administering an IL-6 inhibitor, thereby completing the present invention.

That is, the present invention provides a drug for preventing and treating diseases caused by fibrinoid formation or thrombus formation in the lung, which comprises an inhibitor of interleukin 6 as an effective ingredient. The present invention also provides a model rat of the diseases caused by fibrinoid formation or thrombus formation in the lung, in which fibrinoid formation or thrombus formation in the lung actually occurs by exogenous administration of IL-6.

By the present invention, a drug which can prevent and treat a disease caused by fibrinoid formation or thrombus formation in the lung was first provided Further, by the present invention, a model animal for the disease caused by fibrinoid formation or thrombus formation in the lung vascular system was first provided. In the model animal according to the present invention, the mechanism for onset of the disease is different from that in the conventional monocrotaline model, and fibrinoid formation or thrombus formation is caused and right ventricular hypertrophy is progressed in relation to the dose of IL-6 administered exogenously. Therefore, the model animal provided by the present invention is suited for clarifying the pathologic state of pulmonary heart disease and for studying effective therapeutic modelity of pulmonary heart disease.

BEST MODE FOR CARRYING OUT THE INVENTION

Figure 1:
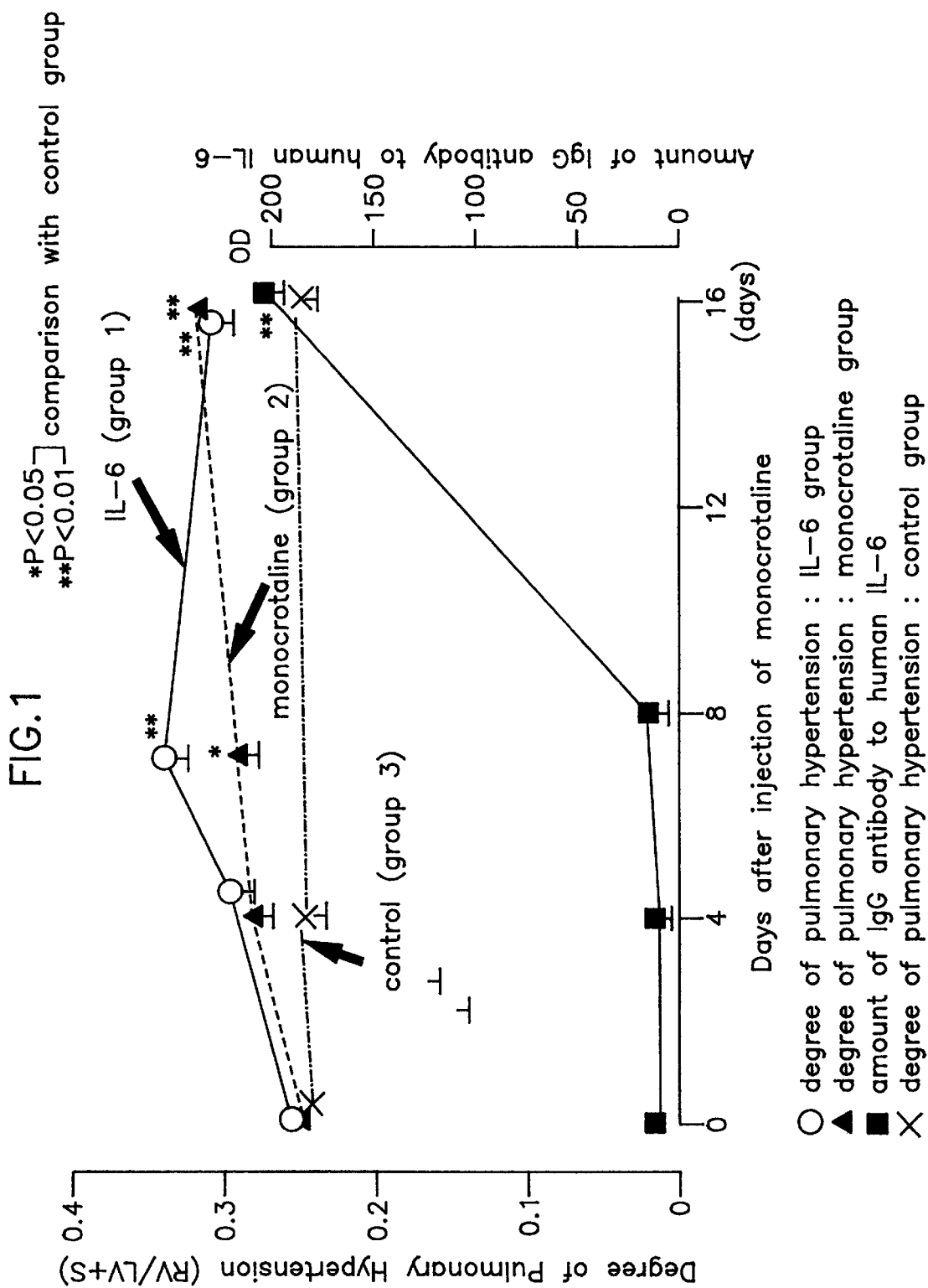
FIG. 1 shows wet weight ratio of right ventricle/(left ventricle+septum) of isolated heart and the amount of IL-6-neutralizing antibody in Example 1.
Figure 2:
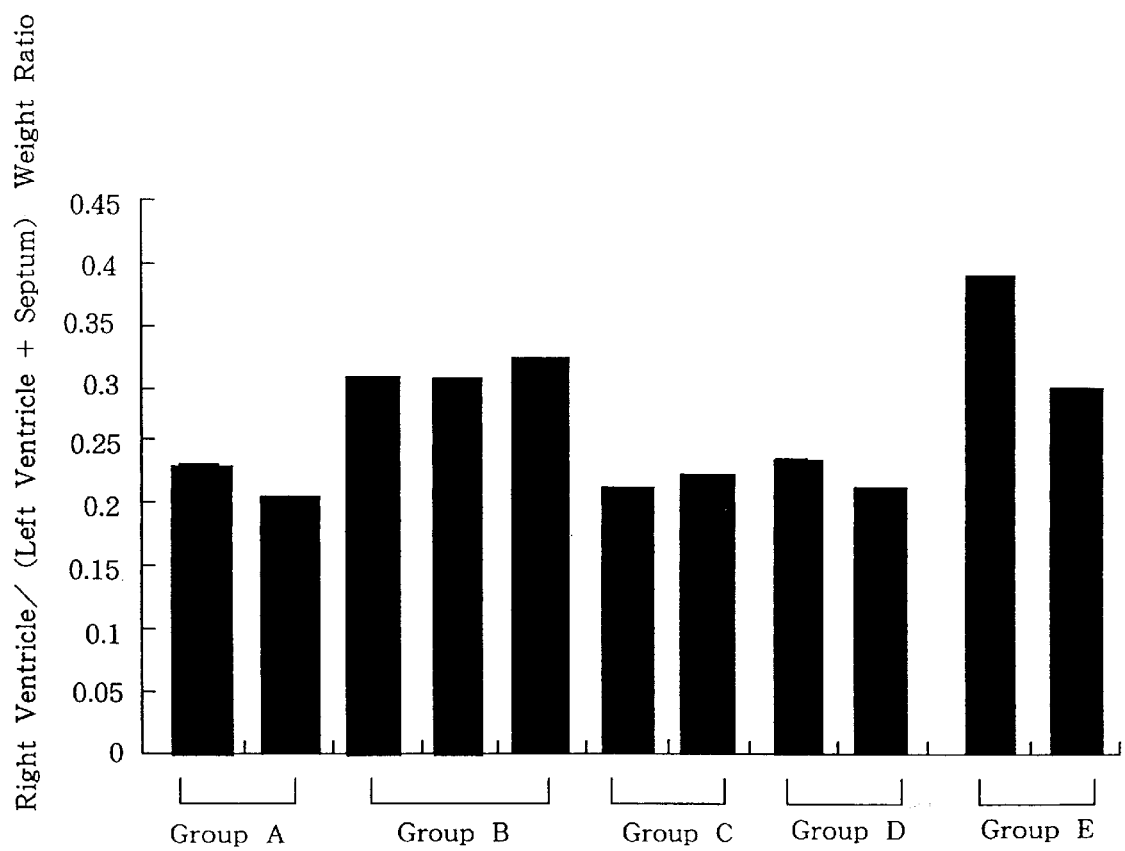
FIG. 2 shows wet weight ratio of right ventricle/(left ventricle+septum) in each group in Example 2.

The present inventors discovered that by administering IL-6 to rats, fibrinoid formation and thrombus formation in the lung are caused to present right ventricular hypertrophy, and pulmonary heart disease is caused. On the other hand, by administering to rats an IL-6-neutralizing antibody together with IL-6, right ventricular hypertrophy was not developed and onset of pulmonary heart was prevented. The present inventors confirmed that by continuously administering human IL-6 to rats, antibody which neutralizes IL-6 of human origin is produced and that the right ventricular hypertrophy is reduced with the increase in the amount of the produced neutralizing antibody, and the development of pulmonary heart disease is inhibited with the increase in the amount of anti-human IL-6 antibody produced in the rats, thereby discovering the therapeutic effect of anti-IL-6 antibodies. The present inventors also discovered preventive effect of anti-IL-6 antibody by observing the fact that onset of pulmonary heart disease is prevented by administering an anti-human IL-6 antibody simultaneously with the administration of human IL-6, thereby completing the present invention.

Any disease characterized by fibrinoid formation or thrombus formation in the lung may be prevented or treated by the drug according to the present invention. Thus, causal diseases of pulmonary heart may also be prevented or treated. Examples of such diseases include pulmonary thromboembolism, pulmonary embolism, chronic occlusive pulmonary disease, pneumoconiocis, various interstitial pulmonary diseases pulmonary hypertension and the like, although the diseases are not restricted thereto.

The drug according to the present invention comprises an IL-6 inhibitor as an effective ingredient. The IL-6 inhibitor is a substance which neutralizes the action of IL-6 or which reduces or inhibits production of IL-6. Examples of the IL-6 inhibitor include IL-6-neutralizing antibodies; $PGE_1$ and its derivatives; $PGI_2$ and its derivatives such as beraprost or the like; and immunosuppressive agents such as cyclophosphamide.

As the IL-6-neutralizing antibodies, both polyclonal antibodies and monoclonal antibodies may be employed, and monoclonal antibodies are preferred. An example of the anti-IL-6 antibodies which have abilities to neutralize IL-6 is IG61 described in Japanese Laid-open Patent Application (Kokai) No. 3-139292 and in European Patent Publication 0 399 429 A1, although the IL-6-neutralizing antibody is not restricted to this antibody. IG61 was deposited in National Institute of Bioscience and Human-Technology, Agency of Industrial Science and Technology at 1–3, Higashi 1-chome, Tsukuba-shi, Ibaraki-ken, Japan, under accession number FERM BP-2878 on Apr. 27, 1990.

The drug according to the present invention may comprise an IL-6 inhibitor alone or may further comprise one or more pharmaceutically acceptable carriers or additives. Examples of such carriers and additives include water, organic solvents such as ethanol, collagen, polyvinylalcohol, polyvinylpyrrolidone, carboxyvinyl polymers, sodium carboxymethyl cellulose, sodium polyacrylate, sodium alginate, water-soluble dextrane, sodium carboxymethyl starch, pectin, methyl cellulose, ethyl cellulose, xanthane gum, gum arabi, casein, gelatin, agar, polyethylene glycol, diglycerin, glycerin, propylene glycol, polyethylene glycol, Vaseline, paraffin, stearyl alcohol, stearic acid, human serum albumin, mannitol, sorbitol, lactose, surfactants and the like.

Additives may be selected from those described above depending on the formulation of the therapeutic agent according to the present invention, although the additives are not restricted to those described above.

The above-described therapeutic agent may be administered together with one or more other drugs simultaneously or sequentially. Such other drugs may be selected from therapeutic drugs for primary diseases, therapeutic agents for right heart failure, such as digitalis, diuretics and the like, anticoagulants, vasodilators, serotonin antagonists, immunosuppressive agents and pharmaceuticals which reinforce the activity or aid the function of the drug of the present invention.

Method for administering the drug is not restricted, and an appropriate administration method is selected depending on the purpose. Formulations for external application and injection are preferred. Formulations for external application include powder and spray, which are administered through the lung, although the formulations are not restricted thereto. An appropriate method for administering injection formulations is selected from intravenous injection, subcutaneous injection, intramuscular injection, intravenous drip infusion, intraperitoneal injection and the like. The drug may also be formulated as a sustained release preparation such as indwelling osmotic pump.

Dose of administration of the IL-6 inhibitor such as an IL-6-neutralizing antibody may preferably be selected from the range of 0.001 mg to 100 mg, more preferably 0.01 mg to 10 mg per 1 kg of body weight per day. Since the dose of administration differs depending on the symptom, the dose of administration is not restricted to the range mentioned above. The drug may be administered once or twice a day, or once per two or several days, although not restricted thereto.

A specific example of the composition of the drug according to the present invention is shown below, although the composition is not restricted thereto.

| IL-6-neutralizing Antibody | 50 mg |
|---|---|
| Physiological Saline | 1 ml |

As mentioned above, the present invention provides a model rat of the diseases caused by fibrinoid formation or thrombus formation in the lung, in which fibrinoid formation or thrombus formation in the lung is actually induced by administration of interleukin 6. IL-6 was first identified as a differentiation factor for maturation of B cells into antibody-producing cells. Since its cDNA was cloned in 1986 (Hirano, T. et al.: Nature, 324, 73–76, 1986), it has been clarified that IL-6 concerns with causes and pathologic states of various diseases (Kishimoto, T.:Blood 74: 1–10, 1989, Kawano, M. et al.:Nature 332: 83–85 1988, Yee, C. et al.:Blood 74: 798–804, 1989, Everson, M. R., et al.: Blood 74: 1472–1476, 1989, Yoshizaki, K. et al.:Blood 74: 1360–1367, 1989, Najima, K. et al.: J. Immunol. 142: 531–536, 1989, Horii, Y. et al.: J. Immunol. 143: 3949–3955, 1989). However, so far, IL-6 has not been reported to cause fibrinoid formation or thrombus formation so as to cause right ventricular hypertrophy, and to relate to onset of pulmonary heart disease.

The present inventors confirmed that actual administration of IL-6 to rats induces fibrinoid formation and thrombus formation as well as right ventricular hypertrophy resulting in pulmonary heart disease, thereby completing the present invention. The extent of right ventricular hypertrophy in our model was about the same as that caused in the monocrotaline-rat model, in the monocrotaline-rat model, hyperplasia of media of muscular pulmonary artery, muscularization of pulmonary arteriole and hyperplasia of intraalveolar septa wall are pathologically observed, while in the model according to the present invention, fibrinoid formation and thrombus formation are caused in the lung, so that the mechanisms of onset of the diseases are different. Further, in the monocrotaline rat model, interstitial pneumonia is complicated while in the model according to the present invention, complication with interstitial pneumonia is not observed. Further, when monocrotaline is administered, right ventricular hypertrophy is observed irrespective of the dose of administered monocrotaline, while in the model according to the present invention, the extent of right ventricular hypertrophy increases dose-dependently with the dose of administered IL-6. Thus, the model according to the present invention is suited for clarifying pathologic state of pulmonary heart and for studying effective therapeutic method of pulmonary heart.

The model rat according to the present invention may be used as a model of any diseases caused by fibrinoid formation and thrombus formation in the lung. Examples of these diseases include the diseases described above.

The model rat according to the present invention may be produced by administering IL-6 to a rat. The type and species of IL-6 used here is not restricted and mammalian IL-6 which is obtained by a known method may preferably be employed. For example, IL-6 obtained by culturing IL-6-producing cells and recombinant IL-6 obtained by genetic recombination method may be employed. The term "IL-6 obtained by culturing IL-6-producing cells" means the IL-6 obtained by culturing mammalian cells. As the mammalian cells, fibroblast cells, endothelial cells, stromal cells and the like may preferably be employed, although the mammalian cells are not restricted thereto. A method for culturing the cells and for purifying IL-6 is described in Japanese Laid-open Patent Application (Kokai) No. 5-176788, although the method is not restricted thereto.

On the other hand, recombinant IL-6 may be produced by a known method using *Escherichia coli* (e.g., Japanese Laid-open Patent Application (Kokai) No. 63-157996. Recombinant IL-6 may also be produced by introducing IL-6 gene into prokaryotic cells such as *Bacillus subtilis*; yeast cells; mammalian cells such as hamster cells, mouse cells, monkey cells and human cells; insect cells; or insects, in addition to *E. coli* cells. The IL-6 gene may be introduced into a host by ligating the IL-6 gene to the downstream region of a promoter which functions in the host and the resultant may be introduced in the form of a DNA or virus.

Induction of the disease in a rat may preferably be attained by administering IL-6 to the rat by an appropriate method such as intravenous injection, subcutaneous injection, intramuscular injection, intravenous drip infusion, intraperitoneal injection or the like. IL-6 transgenic animals produced by a known method may also be used in the present invention. Methods for producing the IL-6 transgenic animals are described in Suematsu, S. et al., (Proc. Natl. Acad. Sci. USA 86: 7547–7551, 1989) and Japanese Laid-open Patent Application (Kokai) No. 5-48093, although the methods are not restricted thereto.

Effective dose of administration of IL-6 to an animal is selected from the range from 0.0001 $\mu$g to 500 $\mu$g, preferably from 0.01 to 300 $\mu$g per day per 1 kg of body weight. Needless to say, since the dose of administration varies depending on the experimental conditions, the dose of administration of IL-6 is not restricted to the range mentioned above. IL-6 may be administered once or twice a day, or once per two or several days, although not restricted thereto. Usually, by continuing the above-mentioned administration for 7–14 days, fibrinoid formation or thrombus formation occurs in the lung.

The present invention will now be described by way of examples thereof. However, the examples described below are presented for the illustration purpose only and should not be interpreted in any restrictive way.

EXAMPLE 1

Production of Pulmonary Heart Disease Model by Administration of IL-6

1. Methods
    1) Sprague-Dawley rats (6 weeks old, male, body weight: 150–200 g, FUNABASHI NOJO, Sendai, Miyagi-ken, Japan) were used. Sixty rats were arbitrarily separated as follows into groups each of which consists of 15 rats. IL-6 was obtained by culturing human fibroblast cells and purifying the produced IL-6 by the method described in Japanese Laid-open Patent Application (Kokai) No. 5-176788.
    Group 1: group to which IL-6 was administered (200 $\mu$g/kg/day, 16 days, s.c.)
    Group 2: group to which monocrotaline was administered (40 mg/kg, the first day only, s.c.)
    Group 3: control group (physiological saline, 16 days, s.c.)
    2) Observation was performed on Day 0, 4, 8 and 16. On each observation day, five rats were arbitrarily selected from each group and observed for the following items
    3) Observation Items
    (1) The degree of pulmonary hypertension was evaluated based on the wet weight ratio of right ventricle/(left ventricle+septum) in accordance with Fulton et al., (Brit. Heart J. 14: 413–420, 1952).
    (2) Pathological observation of the lung tissues was carried out after preparing samples by a conventional fixation method followed by staining the samples with hematoxylin-eosin or Masson-Trichrome. Immunopathological observation for checking the existence of the change in growth of endothelium and inner cavity of blood vessels was performed on the samples stained with BrdU in accordance with Gratzner (Science 218: 474–475, 1982).
    (3) Quantification of IL-6-neutralizing Antibody
    ① An ELISA plate (Dynatech Laboratories Inc., USA) was coated with IL-6 (1 $\mu$g/ml, 0.05 M carbonate bicarbonate buffer, pH9.6) and the resulting plate was incubated at 37° C. for 3 hours and then at 4° C. for 24 hours.
    ② The plate was washed three times with phosphate buffer (0.1 M PBS-T, pH7.4) containing 0.05% Tween 20, and then PBS (PBS-BSA) containing 3% bovine serum albumin (BSA) was added.
    ③ A serum sample diluted 1:50 with PBS-BSA was added in the wells and the plate was incubated at 37° C. for 1 hour, followed by washing three times with PBS-T.
    ④ Alkaline phosphatase-conjugated anti-rat IgG rabbit antibody F(ab')$_2$ diluted 1:1000 with PBS-BSA was added in the wells and the plate was incubated for 1 hour.
    ⑤ After washing the wells three times with PBS-T, nitrophenyl phosphate solution (Sigma Diagnostics, USA, carbonate bicarbonate buffer 0.05 M, pH 9.8) was added to the wells and the absorbance at 405 nm was measured.
2. Results
    1) Weight Ratio of Right Ventricle/(Left Ventricle+Septum)
    As shown in FIG. 1, the weight ratio of right ventricle/(left ventricle+septum) of Group 1 was significantly higher than that of Group 3 at all of the observation days. There was no significant difference in the weight ratio between Group 1 and Group 2.
    2) Histological Observation of Lung
    In Group 1, on and after Day 4, fibrinoid formation and thrombus formation were observed in pulmonary arteriole vessels and in capillary blood vessels. In Group 2, hyperplasia of tunica media of muscular pulmonary artery and infiltration of cells into adventitious tunica of muscular pulmonary artery were observed. Growth of BrdU(+) cells was observed in Group 2 alone, and there was no difference between Group 1 and Group 3.
    3) Amount of IL-6-neutralizing Antibody
    In Group 2, the amount of IL-6-neutralizing antibody was less than the detectable limit at all days on which the antibody was measured, while in Group 1, the amount of the antibody increased on and after Day 8 (FIG. 1).

As shown in FIG. 1, during the process of daily administration of IL-6 for 16 days, the right ventricle/(left ventricle+septum) ratio increased with time as measured on Day 4 and Day 7, so that progress of pathologic state was observed. However, during Day 8 to Day 16, the progress of the disease was stopped or the state of the disease was improved. On the other hand, in the group to which monocrotaline was administered, progressive aggravation of the pathologic state is observed linearly up to Day 16 after administration. Since the administered IL-6 was human species, production of anti-human IL-6 antibody caused by administration of IL-6 to different species was theoretically expected. Thus, the amounts of anti-IL-6 antibodies in the reserved sera of each group were measured. As a result, increase in the titer of anti-human IL-6 antibody from Day 8 to Day 16 was certainly observed. From the above, it is apparent that the stop of progress or improvement of the pathologic state was in commensurate with the production of anti-human IL-6 antibody. The fact that anti-human IL-6 antibody was effective even after onset of the disease clearly indicates the therapeutic effects of the compounds which suppresses production or actions of IL-6.

EXAMPLE 2

Experiments of Neutralization by Anti-IL-6 Antibody

To check whether a compound which suppresses production or actions of IL-6 prevents onset of the disease, we carried out experiments in which anti-IL-6 antibody is administered simultaneously with administration of IL-6. Anti-human IL-6 rat antibody was prepared as follows. That is, IL-6 was subcutaneously administered to the rats used in Example 1 with a dose of 200 $\mu$g/kg. Two weeks later, blood wag collected from the rats and ammonium sulfate was added to the sera to a concentration of 30%. The generated precipitates were collected and dialyzed against PBS. The thus obtained fraction (containing anti-IL-6 polyclonal antibody) is hereinafter referred to as the immunized IgG fraction. It was confirmed that 20 $\mu$g of this IgG fraction sufficiently neutralizes 25 IU activity of recombinant IL-6.

Eleven rats were grouped into the five groups described below and IL-6 and/or the above-mentioned IgG fraction were administered. IL-6 was subcutaneously administered every day for 7 days and the IgG fraction was intravenously administered for 7 days. The immunized IgG fraction was administered simultaneously with the administration of IL-6. As control groups, a group (Group A) to which neither IL-6 nor IgG was administered and a group (Group E) to which intact IgG fraction of the serum of a normal red (a rat not immunized with IL-6) in place the above-described immunized IgG were also provided. Heart was removed on the 7th day after the beginning of administration and the right ventricle/(left ventricle+septum) weight ratio was measured. In the groups to which IL-6 was administered, the dose of administered IL-6 was 200 $\mu$g/kg/day in all cases.

Group A: non-treated group (individuals to which neither IL-6 nor IgG was administered)

Group B: group to which IL-$^6$ alone was administered

Group C: group to which bath IL-6 and the immunized IgG fraction were administered (dose of administration of the IgG fraction was 20 mg/kg/day)

Group D: group to which both IL-6 and the immunized IgG fraction were administered (dose of administration of the IgG fraction was 2 mg/kg/day)

Group E: group to which both-IL-6 and intact IgG fraction from normal rat serum were administered (dose of administration of the IgG fraction was 20 mg/kg/day)

The results are shown in FIG. 1. As shown in FIG. 1, in evaluation on Day 7, induction of pulmonary hypertension had been clearly induced in the group (Group B) to which IL-6 alone was administered in comparison with the non-treated group (Group A). This is the reproduction of the results in Example 1. By administering the anti-IL-6 antibody-containing IgG fraction at a dose of 20 mg/kg/day simultaneously with the subcutaneous administration of IL-6, onset of pulmonary hypertension was completely prevented (Group C). Even when the dose of the anti-IL-6 antibody was 1/10, the administration of anti-IL-6 antibody was effective (Group D). In contrast, in the group (Group E) to which IgG fraction obtained from normal rat was administered in addition to IL-6, onset of pulmonary hypertension was not prevented.

We claim:

1. A method for treating a disease caused by fibrinoid formation in the lung, which comprises:

administering to a subject having such a disease, an effective amount of an inhibitor of interleukin 6 for preventing or treating said disease.

2. The method of claim 1, wherein said inhibitor of interleukin 6 is an antibody which neutralizes interleukin 6.

3. The method of claim 1, wherein said disease caused by fibrinoid formation is pulmonary heart disease (cor pulmonale).

4. The method of claim 3, wherein said pulmonary heart disease is acute pulmonary heart disease, subacute pulmonary heart disease or chronic pulmonary heart disease.

5. The method according to claim 2, wherein said antibody is a monoclonal antibody.

6. The method of claim 1, wherein said inhibitor reduces or inhibits production of IL-6.

7. The method of claim 1, wherein said inhibitor neutralizes IL-6 activity.

8. The method of claim 1, wherein said inhibitor is $PGE_1$ or a derivative thereof.

9. The method of claim 8, wherein said inhibitor is $PGE_1$.

10. The method of claim 1, wherein said inhibitor is $PGI_2$ or a derivative thereof.

11. The method of claim 10, wherein said inhibitor is $PGI_2$.

12. The method of claim 1, wherein said inhibitor is beraprost.

13. The method of claim 1, wherein said inhibitor is an immunosuppressive agent.

14. The method of claim 13, wherein said inhibitor is cyclophosphamide.

15. The method of claim 2, wherein said antibody is a polyclonal antibody.

16. The method of claim 2, wherein said antibody is IG61 (FERM BP-2878).

17. The method of claim 1, wherein a dose of administration of said inhibitor is in a range of 0.001 mg to 100 mg per 1 kg of body weight per one day.

18. The method of claim 17, wherein the dose of administration of said inhibitor is in a range of 0.01 mg to 10 mg per 1 kg of body weight per one day.

* * * * *

Disclaimer

6,083,501 — Masayuki Miyata, Fukushima, Japan; Reiji Kasukawa, Fukushima, Japan; Masanobu Naruto, Kamakura; Nobutaka Ida, Kamakura, Japan; Yu-ichiro Sato, Kamakura, Japan; Katsuaki Kojima, Yokohama, Japan; Nobuo Ida, Machida, all of Japan. DRUG FOR PREVENTION AND THERAPY OF DISEASES CAUSED BY FIBRINOID FORMATION OR THROMBUS FORMATION IN THE LUNG AND MODEL ANIMALS OF THE DISEASES. Patent dated July 4, 2000. Disclaimer filed Feb. 14, 2005, by the assignee. Toray Industries, Inc.

Hereby enters this disclaimer to claims 10, 11 and 12 of said patent.

*(Official Gazette May 17, 2005)*